006!# United States Patent [19]

Trobisch et al.

[11] 3,980,432

[45] Sept. 14, 1976

[54] PARTIAL THROMBOPLASTIN, ITS USE AS DIAGNOSTIC AGENT AND PROCESS FOR PREPARING IT

[75] Inventors: Heiner Trobisch, Dusseldorf; Horst Schwinn, Marbach, Marburg an der Lahn, Germany

[73] Assignee: Behringwerke Aktiengesellschaft, Marburg an der Lahn, Germany

[22] Filed: July 28, 1975

[21] Appl. No.: 599,365

Related U.S. Application Data

[63] Continuation-in-part of Ser. No. 456,892, April 1, 1974, abandoned.

[30] Foreign Application Priority Data

Apr. 2, 1973  Germany............................ 2316430

[52] U.S. Cl................................ 23/230 B; 424/95; 424/101; 424/105
[51] Int. Cl.².................. A61K 35/50; G01N 33/16
[58] Field of Search................ 23/230 B; 195/103.5, 195/99, 66 B, 63; 252/408; 424/2, 95, 101, 105

[56] References Cited

UNITED STATES PATENTS

| 2,687,980 | 8/1954 | Blanchard et al. | 424/95 X |
| 2,923,665 | 2/1960 | Hagan et al. | 195/66 B |
| 3,183,159 | 5/1965 | Singher et al. | 195/63 |
| 3,862,314 | 1/1975 | Zwisler et al. | 424/95 X |

OTHER PUBLICATIONS

R. L. Searcy, Diagnostic Biochemistry, McGraw-Hill, 1969, pp. 123, 124, 214–216 relied on.

*Primary Examiner*—Robert M. Reese
*Attorney, Agent, or Firm*—Curtis, Morris & Safford

[57] ABSTRACT

The present invention relates to a process for preparing partial thromboplastin which comprises extracting bloodless dry placentae with an organic solvent, separating the extract from the undissolved substance, evaporating, dispersing the residue in water and adding, if desired, a stabilizer and/or lyophilizing. It further relates to the partial thromboplastin thus obtained and to its use as diagnostic agent.

6 Claims, No Drawings

PARTIAL THROMBOPLASTIN, ITS USE AS DIAGNOSTIC AGENT AND PROCESS FOR PREPARING IT

The present application is a continuation-in-part of U.S. Pat. application Ser. No. 456,892 filed Apr. 1, 1974 and now abandoned.

The present invention relates to a partial thromboplastin, to its use as diagnostic agent and to a process for preparing it.

In order to detect diagnostically hemorrhagic abnormalities a substance named "thromboplastin" is used for the catalytical conversion of prothrombin into thrombin. There are two different substances, complete and partial thromboplastin: The complete thromboplastin is used to prove factor II-, V-, VII-, and X-deficiency, whereas the partial thromboplastin serves for the diagnosis of hemophilia A (factor VIII-deficiency) and hemophilia B (factor IX-deficiency) as well as for rarer factor XI and factor XII deficiencies.

For preparing the partial thromboplastin organic extracts of animal brains and dry thrombocytes of human origin are used. The chemical composition of the partial thromboplastins obtained from these basic substances is very different. Furthermore, differences appear with regard to the sensitivity in the detection of factor VIII-, IX-, XI and XII deficiencies. The partial thromboplastin from animal brains is always less sensitive. It is therefore desirable to use the more sensitive dry thrombocytes as starting material for the preparation of partial thromboplastin. These substances, however, are available only in limited amounts; but the need for partial thromboplastin is increasing.

Now, a process for preparing partial thromboplastin has been found, which comprises extracting bloodless dry placentae with an organic solvent, separating the extract from the undissolved substance, evaporating, dispersing the residue in water and adding, if desired, a stabilizer and/or lyophilizing.

The invention further relates to the partial thromboplastin thus obtained and to its use as diagnostic agent.

It has not yet been known how to extract from placentae a partial thromboplastin which is suitable as a diagnostic agent. The placentae used as starting material are preferably to be of human origin. On principle, animal placentae are also suitable for the process of the invention, but the product extracted from human placentae is preferred due to its superior properties.

To facilitate the extraction it is suitable to comminute the placentae first. The placentae have to be freed from blood, preferably by washing, in order to remove the coagulable phosphatides in the blood and other constituents soluble in organic solvents, which may have disturbing effects in the product. In order to avoid that disturbing constituents pass into the extract, it is furthermore necessary to extract the placenta material in a dry state.

As organic solvents suitable for the extraction there come into consideration all solvents which can be used to dissolve phospholipides. The main groups of such solvents are halogenated hydrocarbons and cyclic ethers.

Among the halogenated hydrocarbons the preferred group comprises halogenated lower alkanes bearing one or more halogen atoms preferably chlorine, bromine. The most convenient solvents of this class are those which have a boiling point in the range between about 40° and about 150°C. Solvents having a lower or higher boiling point are likewise suitable, however, they are less convenient. Especially suitable solvents are for example ethyl bromide, ethyliodide, propylchloride, propylbromide, propyliodide, butylchloride, methylene chloride, methylene bromide, chloroform, bromoform, carbon tetrachloride, ethylene chloride, ethylidene chloride, ethylidene bromide, tetrachloroethane, trimethylene bromide or isopropylchloride.

Among the cyclic ethers the 5- or 6- membered cyclic mono- or di-ethers are preferred particularly such having boiling points between about 40° and 150°C. Preferred ethers of this kind are for example tetrahydrofuran, dioxane, tetrahydropyran.

The extracting agent is used in an amount which corresponds to about 20 to 100 times the amount of the dried placenta material (volume/weight). The amount is expediently divided into several portions being used successively in several extraction steps. In this case the extracts are preferably combined to be further worked up, but it is also possible to separately work up the extract of each individual extraction step. The use of different extracting agents in the individual extraction steps is also possible.

The extraction of the placentae is expediently carried out at a moderately elevated temperature, e.g. between room temperature and 80°C, for example in the case of solvents having a low boiling point such as chloroform or tetrahydrofurane at their boiling point.

As stabilizers for the finished product are considered all substances known for this purpose. As examples may be mentioned filling agents such as carbohydrates (e.g. lactose, saccharose, dextran up to a molecular weight of about 5,000), polyethyleneglycol or albumin; buffer substances such as glycin or antioxydants such as gallic acid esters, for example gallic acid butyl ester or ascorbic acid.

To improve the storage capacity, drying of the product of the invention is recommended. It has proved particularly advantageous to fill the solution obtained according to the invention in determined amounts into small flasks as to dry it therein, for example by lyophilization.

The process of the invention may be carried out in the following way: The ground placentae, washed free from blood with a physiological sodium chloride solution and lyophilized, are extracted at room temperature several times, for example 3 times with an excess, for example about 20 times the weight, with a solvent such as chloroform. The present process may also be carried out at higher temperatures even up to the boiling point of the chloroform, expediently in a Soxhlet apparatus without the activity of the product of the invention being decreased. The volume of the solvent necessary for extraction may be reduced according to the degrees of the temperature. The extract obtained after the extraction by removing the unsoluble part is evaporated, for example in the rotation evaporator. A wax-like yellow residue is formed. The wax-like residue is dispersed in a concentration of 0.025–0.2 % (w/v) preferably of 0.1 %, in distilled water, preferably with a rotation homogenizer. Stabilizers may be added to the lipid dispersion. Apart from the substances already mentioned there may also be used sugar alcohols, e.g. mannite, sorbite, inosite or sodium glutaminate. 1–5 % of sugar alcohols and 0.2–2.5 % of sodium glutaminate are, for example, used. To adjust the pH-value to 7.5–8.4, preferably 8.0, the necessary amount of 1 N sodium hydroxide solution may be added.

The product thus prepared may be filled into rolled rim flasks for storage and dried by lyophilization.

The product prepared according to the invention is redissolved in a 0.2–2 %, preferably in a 0.5 % suspension of kaolin in a diluted, preferably 0.5 % sodium chloride solution, for use as a diagnostic agent.

The product of the invention can be used to determine the partial thromboplastin time (searching test for disturbances in the endogeneous coagulation system), but also for a quantitative determination of the factor VIII-, IX-, XI- and XII activity.

The test for using the product of the invention for the diagnosis of disturbances of the endogeneous coagulation system (partial thromboplastin time) is carried out in the following manner: One part of the lipid-kaolin-suspension is mixed in a small test tube with one part of a normal plasma or pathological plasma, in which the coagulation disturbances are to be determined qualitatively, and incubated for 2 minutes at 37° ± 0.5°C. After addition of a further part of a 0.025 molar calcium chloride solution pre-heated to 37°C the time which passes from the addition of the calcium chloride solution to the appearance of a solid fibrin coagulum is measured. If the coagulation time of the pathological plasma is longer than that of the normal plasma (35–50 seconds) then there is a disturbance in the activity of the endogeneous coagulation system (factor VIII-, IX-, XI and XII- deficiency). The condition for this statement is that other qualitative tests (Quick-value and plasmathrombin time) show normal coagulation times.

The test for using the product of the invention to determine the factor VIII-, IX-, XI and XII activity (quantitatively) is carried out in the following way:

1 Part of the lipid-kaolin-suspension is mixed in a small test tube with one part of factor VIII-, IX-, XI or XII-deficiency plasma and with 1 part of diluted normal plasma or pathological plasma. This mixture is maintained for 6 minutes at 37°C. After adding 1 part of a 0.025 molar calcium chloride solution pre-heated to 37°C, the time which passes from the addition of the calcium chloride solution to the appearance of a solid coagulum is measured.

For a quantitative statement the coagulation time resulting from the diluted pathological plasma is read from a calibration curve obtained with a normal plasma dilution series. Normally the content of factor VIII is 80–200 %
factor IX is 80–150 %
factor XI is 80–150 %
factor XII is 80–120 % calculated on normal plasma.

The following examples illustrate the invention:

EXAMPLE 1

10 kg of frozen human placentae were comminuted with the aid of a mincer. The placentae homogenate was washed at +10°C 16 to 18 times with 90 liters of a 0.9 % sodium chloride solution each time, and with each washing process the washing water was eliminated by sedimentation and decantation. The last supernatant was colorless. The placentae homogenate washed in this way was freed from the remaining washing water for 30 minutes by centrifugation at 3,000 g. The moist sediment was dried for 30 hours in a closed freeze-drying device up to a residual moisture of 5%. The yield of the dry material was about 900 g.

For two days the dry product was extracted three times, while stirring, with 18 liters of cold chloroform in each case. Between the extractions the unsoluble residue was isolated by filtration. The extracts were collected, concentrated with water-jet vacuum at 50°C in the rotation evaporator until a yellow wax-like residue appeared. The yield was 80 g of the partial thromboplastin.

One gram of the product obtained in this way was dispersed at room temperature in 1 liter of distilled water with the aid of a rotation homogenizer. Then 40 g of mannite and 10 g of sodium glutaminate were dissolved while stirring in the lipid dispersion. The pH-value was adjusted to 8.0 with a 1 N sodium hydroxide solution under the glass electrode. The product was stirred for 1 hour at 37°C. It was filled into rolled rim flasks in portions of 1 ml and dried for 24 hours by lyophilization.

EXAMPLE 2

70 Grams of the dry intermediate product obtained according to example 1 were extracted for 2 hours in the Soxhlet apparatus with 1.4 liters of chloroform at the boiling point of the chloroform (61.5°C). The extract obtained was further worked up according to example 1. The yield of the product of the invention was 6.4 g.

Under the conditions of Example 1 or 2 a partial thromboplastin was also obtained if instead of chloroform the following halogenated hydrocarbons were used: Ethyl bromide, ethyl iode, propyl chloride, propyl bromide, propyl iodide, butyl chloride, methylene chloride, methylene bromide, chloroform, bromoform, hydrocarbon tetrachloride, ethylene, chloride, ethylidene chloride, ethylidene bromide, tetrachloro-ethane (symmetrical), trimethylene bromide, isopropyl chloride. As cyclic ethers there were used tetrahydrofurane, dioxane and tetrahydropyrane. The extraction had to be carried out according to Example 2 at the corresponding boiling point of the solvent, if desired under reduced pressure.

What we claim is:

1. A process for preparing a partial thromboplastin which comprises extracting bloodless dry comminuted placentas with an organic solvent selected from the group consisting of halogenated hydrocarbons and cyclic ethers in an amount from 20 to 100 times the weight of the placentas and at a temperature between room temperature and 80°C, separating the extract from the undissolved placental residue, evaporating the solvent from the extract, and dispersing the resulting residue in water to yield a concentration of 0.025 to 0.2 percent.

2. Process of claim 1 wherein the organic solvent is chloroform.

3. Process of claim 1 wherein the organic solvent is tetrahydrofurane.

4. A process for preparing a partial thromboplastin which comprises adding a lipid dispersion stabilizing agent to the product of claim 1, said agent being selected from the group of carbohydrates, polyalcohols, buffer substances, antioxidants, and albumin, and then lyophilizing the mixture.

5. A process for preparing a diagnostic agent useful in the evaluation of disturbances of the coagulation system, which comprises dissolving the product of claim 4 in a 0.2 to 2 percent suspension of kaolin in an about 0.5 percent sodium chloride solution.

6. A process for the evaluation of the partial thromboplastin time, which comprises mixing one part by volume of the product of claim 5 with one part by volume of plasma, keeping the mixture for 2 minutes at 37° ± 0.5° C, subsequently adding one part by volume of a 0.025 molar calcium chloride solution and measuring the resulting clotting time.

* * * * *